United States Patent [19]

Chapman et al.

[11] Patent Number: 5,380,904
[45] Date of Patent: Jan. 10, 1995

[54] PROCESS FOR RENDERING A SURFACE BIOCOMPATIBLE, AND ARTICLES CONTAINING THE SAME

[75] Inventors: Dennis Chapman, Buckinghamshire; Aziz A. Durrani, London, both of England

[73] Assignee: Biocompatibles Ltd., London, England

[21] Appl. No.: 169,641

[22] Filed: Dec. 20, 1993

Related U.S. Application Data

[60] Continuation of Ser. No. 73,662, Jun. 8, 1993, abandoned, which is a division of Ser. No. 789,894, Nov. 12, 1991, Pat. No. 5,299,162, which is a division of Ser. No. 510,840, Apr. 18, 1990, Pat. No. 5,091,551, which is a division of Ser. No. 328,709, Mar. 27, 1989, Pat. No. 4,937,369, which is a continuation of Ser. No. 114,762, Oct. 29, 1987, abandoned, which is a division of Ser. No. 778,185, Sep. 18, 1985, Pat. No. 4,721,800.

[30] Foreign Application Priority Data

Jan. 20, 1984 [GB] United Kingdom ............... 8401534

[51] Int. Cl.$^6$ .................. C07F 9/146; C07F 9/10; A01N 1/02; B01J 16/00
[52] U.S. Cl. .................. 558/166; 558/70; 427/385.5; 427/2.25; 427/2.3; 128/912; 623/1; 623/11; 623/16; 623/66
[58] Field of Search .............. 427/2, 385.5; 128/912; 558/70, 166, 199; 554/80; 522/171; 623/1, 11, 16, 66; 987/233

[56] References Cited

U.S. PATENT DOCUMENTS

| | | |
|---|---|---|
| 3,197,431 | 7/1965 | Lankham et al. . |
| 3,202,633 | 8/1965 | Tekete . |
| 3,492,193 | 1/1970 | Tesoro . |
| 4,006,175 | 2/1977 | Heckert et al. . |
| 4,206,156 | 6/1980 | Kamiya et al. . |
| 4,239,709 | 12/1980 | Sato . |
| 4,348,329 | 9/1982 | Chapman et al. . |
| 4,471,131 | 9/1984 | Franz . |
| 4,609,646 | 2/1986 | Hoffman et al. . |
| 4,640,790 | 2/1987 | Sylvester et al. . |
| 4,792,599 | 12/1988 | Durrani ........................ 528/272 |
| 4,851,009 | 7/1989 | Pinchuk ........................ 623/66 |
| 4,973,493 | 11/1990 | Guire ........................... 427/2 |
| 4,979,959 | 12/1990 | Guire ........................... 623/66 |
| 5,263,992 | 11/1993 | Guire ........................... 623/66 |

FOREIGN PATENT DOCUMENTS

| | | |
|---|---|---|
| 5826893 | 8/1981 | Japan . |
| 1016078 | 1/1966 | United Kingdom . |

OTHER PUBLICATIONS

Kosolapoff et al, "Organic Phosphorus Compounds", 6:227 (1974).

Kodaira et al, *Jrnl. of Organ. Chem.*, 33:2903–2907 (1966).

Kosolapoff et al, "Organic Phosphorus Compounds", *John Wiley & Sons*, vol. 6 (1974).

*Primary Examiner*—Arthur C. Prescott
*Attorney, Agent, or Firm*—Sughrue, Mion, Zinn, Macpeak & Seas

[57] ABSTRACT

A compound of formula:

$$X^1 - \overset{\overset{\displaystyle O}{\|}}{\underset{\underset{\displaystyle X^2}{|}}{P}} - O - (CH_2)_n Y \qquad \text{I}$$

in which $X^1$ is a reactive group that can react to form a covalent bond with a reactive group on the surface of a material to be rendered biocompatible, $X^2$ is a group $-O^{\ominus}$ or a precursor of such a group, n is 2, 3 or 4, Y is a group $-N^{\oplus}R_3 A^{\ominus}$ wherein each R, which may be the same or different, is a $C_1$-$C_4$ alkyl group and $A^{\ominus}$ is an anion present when $X^2$ is an electrically neutral group or Y is $$-\underset{\underset{\displaystyle R^1}{|}}{NH}$$

wherein $R^1$ together with $X^2$ forms a direct bond between the nitrogen and the phosphorus atoms.

9 Claims, No Drawings

PROCESS FOR RENDERING A SURFACE BIOCOMPATIBLE, AND ARTICLES CONTAINING THE SAME

This is a continuation of application Ser. No. 08/073,662, filed Jun. 8, 1993; now abandoned which in turn is a divisional of application Ser. No. 07/789,894, filed Nov. 12, 1991 (now U.S. Pat. No. 5,299,162); which in turn is a divisional of application Ser. No. 07/510,840, filed Apr. 18, 1990 (now U.S. Pat. No. 5,091,551); which in turn is a divisional of application Ser. No. 07/328,709, filed Mar. 27, 1989 (now U.S. Pat. No. 4,937,369); which in turn is a continuation of application Ser. No. 07/114,762, filed Oct. 29, 1987 (now abandoned); which in turn is a divisional of application Ser. No. 06/778,185, filed Sep. 18, 1985 (now U.S. Pat. No. 4,721,800).

This invention relates to biocompatible surfaces and to new compounds useful in the production of such surfaces.

The clinical use of blood contacting devices and prostheses is of major importance today in cardiovascular surgery and other fields of medicine. Heart valves and blood vessel prostheses, balloon pumps and catheters are being implanted in daily surgical practice to restore or diagnose cardiovascular function. Artificial organs are routinely employed in blood detoxification by absorptive haemoperfusion and in oxygenation (membrane oxygenators and heart-lung devices). Considerable effort and capital is invested in Europe and the U.S.A. in the development and experimental evolution of an implantable artificial heart system. The devices are generally constructed from polymeric materials and when in use, a blood-polymer contact is present. This contact will cause a reaction in the recirculating blood, which, depending on the choice of material, the design parameter, the flow or the addition of the anticoagulants, may lead to protein deposition, adhesion and destruction of red blood cells (haemolysis), platelet (thrombocyte) adhesion and aggregation and blood coagulation leading to the formation of a haemostatic plug (thrombus). The occurrence of thromboembolism in cardiovascular surgery continues to be a problem, notwithstanding routine treatment with anticoagulants. For these reasons the search for biocompatible non-thrombogenic materials has been an important research objective over the last two decades.

Our concept is to try to mimic, as far as possible, the interfacial characteristics of the outer cell surface of red blood cells and platelets. The simplest common factor of all these surfaces is the lipid of the biological membrane.

Biological membranes are important in all areas of the body. Every cell has an outer membrane and within the cell there are membranes that act to compartmentalize the various organelles, e.g. the mitochondria, nucleus and endoplasmic reticulum. Membranes are particularly important features of the blood cells, e.g. erthrocytes and leucocytes. The various cell membranes, including those of red blood cells, are all built upon an asymmetric lipid matrix of polar lipids in which the intrinsic proteins are distributed. The outer surface of the lipid matrix consists of both phosphatidyl choline lipids and sphingomyelin lipids. Both of these classes of lipid have the same polar group:

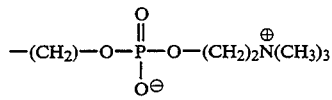

This polar surface is a common feature of the outer surface of red blood cells, platelets, lymphocytes, etc. The inner surface is different and usually contains a predominance of the negatively charged lipids.

In recent years there has been considerable work on the physical chemistry of phospholipids and membranes. (Chapman, D., Q. Rev. Biophys., 8, 185, 1975). Studies of cell systems have shown (Zwaal et al., Nature, 268, 358–360, 1977) that pro-coagulant lipids occur on the inner cell surface but not on the outer surfaces.

Our new approach to this problem is therefore to mimic the lipid polar portion of the cell membrane's outer surface by altering surface characteristics of existing materials, e.g. glasses and polymers by chemical modifications.

The aim is chemically to modify some existing materials so that covalent linkages are formed containing these polar groups. This retains the mechanical properties of the material whilst the interfacial properties are changed to mimic those of membrane surfaces.

In some of our recent studies (Hayward & Chapman Biomaterials, 5, 135–141, 1984) we have examined surface coatings containing the appropriate polar groups. The haemocompatibility of liposomal preparations was estimated by comparing the recalcification clotting times of citrated pooled normal plasma in the presence of assorted lipid dispersions. A brain lipid extract (containing large amounts of negatively charged phospholipids) markedly accelerated the rate of clot formation in a concentration-dependent manner. In contrast, liposomes prepared from dimyristoyl phosphatidylcholine did not reduce the blank clotting times. Similarly, clot formation was not affected by diacetylenic phosphatidylcholine when present in either monomeric or polymeric form. These results support our concept for biocompatible surfaces. It is clear however that covalent linkages of the polar groups to the treated material are necessary for maximum mechanical stability. As far as we are aware, there has been no modification of the type that we are proposing.

We have discovered a group of new compounds which are derivatives or analogues of phosphatidylcholine or phosphatidyl ethanolamine that can be covalently linked to the surface which is to be rendered biocompatible so as to deposit a phosphatidylcholine- or phosphatidyl ethanolamine-type of residue on the surface. New compounds of the present invention are those of the formula:

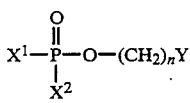

in which $X^1$ is a reactive group that can react to form a covalent bond with a reactive group on the surface of a material to be rendered biocompatible, $X^2$ is a group $-O^\ominus$ or a precursor of such a group, n is 2, 3 or 4, Y is a group $-N^\oplus R_3 A^\ominus$ wherein each R, which may be the same or different, is a $C_1-C_4$ alkyl group and $A^\ominus$ is an anion present when $X^2$ is an electrically neutral group or Y is $$-\underset{\underset{R^1}{|}}{N}H \qquad \qquad 5$$

wherein $R^1$ together with $X^2$ forms a direct bond between the nitrogen and the phosphorus atoms.

In the compounds of the invention, it is preferred that each R represents methyl and that n is 2 so that a phosphatidylcholine residue is introduced onto the surface but analogues and homologues of phosphatidylcholine of the type defined can equally well be introduced. Alternatively, or preferably in combination therewith, a phosphatidyl ethanolamine-type residue is introduced onto the surface.

The exact chemical nature of the group $X^1$ will depend upon the chemical nature of the reactive group on the surface to be rendered biocompatible. Almost all surfaces that one might wish to render biocompatible normally contain free reactive alcoholic hydroxy groups on their surface or are surfaces onto which such free alcoholic hydroxy groups can be readily introduced, e.g. using an alkali metal hydroxide to hydrolyse a surface ester group or halogeno group. Consequently, $X^1$ will normally be a group that will react with an alcoholic hydroxy group to form a covalent link, typically by forming a phosphonic acid ester group from the alcoholic hydroxy group and the phosphonic acid residue of the phosphatidylcholine- or phosphatidyl ethanolamine-type material. Such phosphonic ester groups can be prepared from compounds of the invention in which $X^1$ represents halogen, particularly chlorine although, depending upon the reactivity of the alcoholic hydroxy group, other halogens such as fluorine or bromine can also be used.

As an alternative to the use of halogeno derivatives $X^1$ may also represent a group of the formula;

$$-O-\underset{\underset{R}{|}}{\overset{\overset{R}{|}}{Si}}-X^3 \qquad \qquad II$$

each R, which may be the same or different, represents a $C_1$-$C_4$ alkyl group, preferably both methyl, and $X^3$ represents a group that will react with the reactive group on the surface to be rendered biocompatible with the formation of a covalent linkage. As in the case of $X^1$, the exact chemical nature of $X^3$ will depend upon the nature of the reactive group on the surface to be rendered biocompatible but, for the reasons mentioned above, the reactive group on the surface to be rendered biocompatible will normally be an alcoholic hydroxy group, and, again as mentioned above, this indicates that the group $X^3$ will conveniently be a halogeno group, typically chlorine although again, depending upon the reactivity of the alcoholic hydroxy group, other halogens such as fluorine or bromine can be used.

In a further embodiment of the invention, $X^1$ can represent a group of the formulae:

(c) $-O-(CH_2)_y-OT^1$     III
(d) $-O-(CH_2)_y-NH_2$     IV

-continued $$(e)-O-(CH_2)_y-\underset{\underset{R}{|}}{\overset{\overset{R}{|}}{Si}}-X^3 \qquad \qquad V$$

where y is an integer of 1 to 10 and R and $X^3$ are as defined above.

The group $X^2$ will normally be $-O^{\ominus}$ so that the modified surface carries a phosphatidylcholine- or phosphatidyl ethanolamine-type residue but it is often convenient to have the group $X^2$ in the new compounds of the invention representing a precursor of the $-O^{\ominus}$ group, e.g. halogen such as chlorine so that this precursor group is converted to $-O^{\ominus}$ before, during or after formation of the covalent linkage by the reaction of the group $X^1$.

Anion $A^{\ominus}$ when required to be associated with the new compounds of the invention can be any anion, preferably a biocompatible anion. This anion can be the anion of an inorganic or organic acid and is typically a halide anion such as chloride or alternatively the anion of an alkanoic acid such as acetic acid.

The new compounds of the invention can be prepared by reacting a compound of the formula:

$$Y(CH_2)_n-OH \qquad \qquad VI$$

with a phosphorus oxyhalide e.g. $POCl_3$ to give compounds of the formula I in which $X^1$ represents halogen and, when Y is a group $-N^{\oplus}R_3.A^{\ominus}$, $X^2$ is also halogen. Analogues of phosphorus oxyhalides may be used in order to produce derivatives of formula I in which $X^1$ and $X^2$ represent other reactive groups or alternatively, reaction can first be carried out with phosphorus oxyhalide to give a dihalophosphate and one or both of the halogeno residues can subsequently be converted by methods known per se into other reactive groups so that $X^1$ can react with the reactive group on the surface to be rendered biocompatible with the formation of the covalent link.

Compounds of the invention where $X^1$ represents a group of the formula II as indicated above can be obtained by reaction of a compound of formula VI wherein Y is a group $-NR_3.A$ with e.g. phosphorus oxychloride as indicated above to form a dichlorophosphate of acetylcholine or an analogue thereof. Hydrolysis of the chlorine residues, e.g. by treatment with aqueous sodium bicarbonate or sodium carbonate converts the dichlorophosphate into a derivative of phosphatidylcholine or an analogue thereof of the formula:

$$\underset{\underset{O^{\ominus}}{|}}{\overset{\overset{O}{\|}}{HO-P}}-O(CH_2)_n-\overset{\oplus}{N}R_3 \qquad \qquad VII$$

and this may be reacted with a silane of formula:

$$X^3-\underset{\underset{R}{|}}{\overset{\overset{R}{|}}{Si}}-hal \qquad \qquad IIA$$

where R and $X^3$ are as defined above and hal is a halogeno group to introduce the group II as defined above.

Compounds of the invention wherein Y is a group —N⊕R₃.A⊖ and x¹ is a group of formula III and V can be prepared by reacting a compound of the formula:

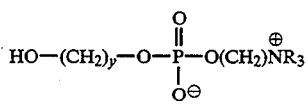   VIII with

T10R   IIIA or IIA respectively.

Compound VIII is prepared by reacting I with an ethyl vinyl ether mono protected diols of formula:

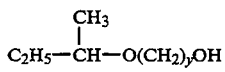   IX followed by removal of the protective group with acidified ice water, concentration and sodium bicarbonate treatment.

Compounds wherein Y is a group —NR₃.A and X¹ is a group of formula IV are prepared by reacting I with an alkanolamine followed by the cleavage of the oxaphospholane X thus formed using aqueous acid followed by a base such as sodium bicarbonate:

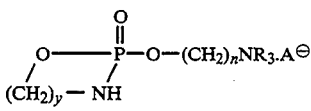   X

Compounds of formula (I) wherein Y is

may be produced in the same manner using appropriate starting materials thus, for instance phosphorus oxychloride reacts with ethanolamine to form 2-chloro-2-oxo-1,2,3-oxazapholane as follows:

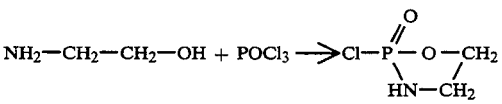

All the compounds of the invention will react with hydroxy groups in the surface to be rendered biocompatible to bind the phosphatidylcholine- or phosphatidyl ethanolamine-type covalently to the surface except compounds of the invention where X¹ is a group of formula III or V which will react with surface halogens and acid chloride groups respectively. In all cases the phosphatidylcholine- or phosphatidyl ethanolamine-type group becomes covalently linked to the surface.

In the case of 2-chloro-2-oxo-1,2,3-oxazapholane which contains a reactive chlorine atom, when brought in contact with an hydroxyl group, this is deposited as follows:

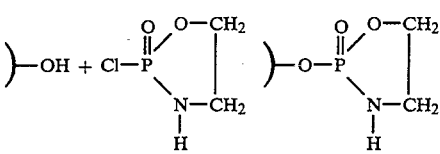

The oxazapholane ring is finally cleaved with dilute acetic acid to obtain the ethanolamine residue:

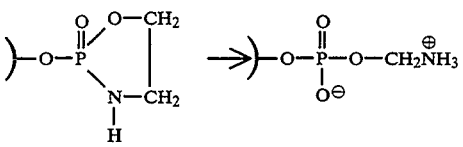

Similar processes may be employed for introducing other phosphatidyl ethanolamine-type groups onto a surface.

In accordance with a further feature of the invention, there is provided a process for rendering a surface biocompatible which comprises applying to the surface a compound of formula I under conditions such that the group X¹ reacts to form a covalent linkage with a reactive group on the surface to be rendered biocompatible.

The compounds of the invention are not very soluble in solvents such as chloroform, petroleum ether, carbon tetrachloride or tetrahydrofuran and tend to react with solvents in which they are appreciably soluble, e.g. water or alkanois, so that it is preferred to use the compounds in undiluted state for the treatment of the surfaces. Although compounds in which X¹ is a group IV do not react with either water or alkanois, the surface acid chloride group (which is meant to react with X¹ in these cases) will react with these solvents.

The present invention is applicable in principle to the treatment of the surface of any prosthesis to be introduced into the human or animal body or any surface which is to be brought into contact with body fluids, e.g. blood on an extra-corporeal basis, cells or tissues in culture. It may also be advantageous to treat surfaces of equipment, especially culture vessels, used in cell and tissue culture, in order to provide biocompatible surfaces. In order to demonstrate the benefit of the present invention, we have carried out experiments with glass, polyvinyl alcohol, perspex, polyhema, cellulose acetate and PTFE surfaces and with surfaces of polymethylmethacrylate which have been surface modified to ensure the presence of alcoholic hydroxy groups in the surface. However surfaces of other materials such as metals, or plastics which are polymers or copolymers based on various polyacrylic or polyvinyl materials and others containing olefinic bonds are also suitable for modification, if necessary after replacing the double bonds by, for example, halogeno, hydroxy or acid chloride groups, in accordance with the present invention.

The following Examples are given to illustrate the invention.

EXAMPLE 1

Preparation of choline acetate dichlorophosphate (I)(a)

$$(CH_3)_3\overset{\oplus}{N}(CH_2)_2OH \cdot {}^{\ominus}OCOCH_3 + POCl_3 \longrightarrow Cl-\underset{\underset{Cl}{|}}{\overset{\overset{O}{\|}}{P}}-O(CH_2)_2\overset{\oplus}{N}(CH_3)_3 \cdot {}^{\ominus}OCOCH_3 \quad [(I)(a)]$$

Phosphorus oxychloride (23 g; 0.15 mole) was dissolved in anhydrous carbon tetrachloride (50 ml), placed in a bath containing ice/salt mixture and was treated with a dropwise addition of acetylcholine (16.3 g; 0.1 mole) over 30 minutes. During this addition, a slow stream of dried nitrogen was passed through the mixture, which was stirred thoroughly throughout the reaction time. After the addition of acetylcholine, the mixture was stirred for an additional hour at 0° C. with continuous nitrogen passage.

The upper layer of the reaction mixture was collected, washed once with anhydrous carbon tetrachloride (50 ml) and was then freed from the volatile matter (40° C., 15 mm Hg) to obtain the yellow oil (I)(a) in more than 70% yield. The substance was highly reactive towards water with the evolution of hydrogen chloride and gradually decomposed on standing but can be stored for up to 3 weeks under dry nitrogen in an air-tight glass container.

EXAMPLE 2

Alternative Preparation of Compound (I)(b)

Acetylcholine dichlorophosphate (Ia) (10 g), obtained as described in Example 1, was placed in an ice bath, stirred and then treated with drops of ice water (10–15 ml). Most of the unreacted water was evaporated (60° C.; 15 mm Hg) the residue dissolved in methanol (40 ml) and treated with solid sodium bicarbonate until no more effervescence was observed. The solid was removed by filtration, washed once with methanol (10 ml) and the solid discarded. The combined filtrate was evaporated to dryness (60° C.; 15 mm Hg) and the residue, which was free from volatile matter, was stored overnight in a vacuum desiccator over phosphorus pentoxide at 0.1 mm.

Phosphatidylcholine, obtained as above, was added dropwise to a vigorously stirred dichlorodimethyl silane (50 ml) over 45 minutes. The HCl gas produced was flushed out by passing a stream of dried nitrogen through the reaction mixture. After the addition of phosphatidylcholine was completed, the mixture was kept stirring for an additional 30 minutes. Volatile matter of the reaction mixture was distilled off (50° C.; 15 mm Hg) which was mostly the unreacted silane with some HCl gas, to obtain (I)(b) as greyish red, viscous, non-volatile matter. It was found to be active towards water.

EXAMPLE 3

Preparation of ethylene glycol phosphatidylcholine (I)(c)

i) Half protected ethyl vinyl adduct of ethylene glycol: (1-Ethoxyethyl-2-hydroxy ethyl ether)

(1-Ethoxyethyl-2-hydroxy ethyl ether)

$$C_2H_5-O-\underset{\underset{H}{|}}{\overset{\overset{CH_3}{|}}{C}}-O-CH_2-CH_2-OH$$

Dried ethylene glycol (124 g; 2 moles) was placed in ice/salt mixture, stirred and treated with a dropwise addition of ethyl vinyl ether (72 g; 1.0 mole) in the presence of p-toluene sulphonic acid (0.25 g) over two hours. the mixture was then stirred for an additional hour at 0° C. The product distilled at 80°–85° C.

ii) Ethylene glycol phosphatidylcholine (I)(c):

Compound (I)(a) (28.1 g; 0.1 mole) was stirred thoroughly and treated with a dropwise addition of 1-ethoxyethyl-2-hydroxyethylether (13.4 g; 0.1 mole) over one hour. External cooling was applied in order to control the temperature at around 15° C. The evolved hydrochloric acid was removed from the reaction mixture by a constant stream of dried nitrogen. When the addition was completed, the mixture was stirred for another 15 minutes at room temperature.

Concentrated hydrochloric acid (2 ml) and crushed ice (100 g) mixture was added and stirring continued. After about 15 minutes stirring the mixture appeared to have increased its temperature as well as become darker in colour. (Larger scale, e.g. 1 mole, reactions became hot at this stage but the temperature must be controlled to around room temperature).

Volatile materials were evaporated (60°–70° C.; 15 mm Hg) and the residue was dissolved in methanol (75 ml). The solution was treated with solid sodium bicarbonate until no more effervescence was noticed. The solid was filtered and was washed with methanol (10 ml). The combined filtrate was evaporated to dryness (70° C.; 15 mm) to free it from all the volatile matter. It was then stored over $P_2O_5$ at 0.1 mm Hg for 24 hours.

EXAMPLE 4

Preparation of Phosphatidylcholine ethylene glycol thallate (I) (d)

$$Tl O-(CH_2)_2-O-\underset{\underset{O^{\ominus}}{\diagdown}}{\overset{\overset{O}{\diagup\!\!\!\!/}}{P}}-O(CH_2)_2\overset{\oplus}{N}(CH_3)_3$$

Ethylene glycol phosphatidylcholine (I) (c) (5.67 g; 0.025 mole) was dissolved in anhydrous absolute alcohol (25 ml), stirred and was treated with thallous ethoxide (6.22 g; 0.025 mole). A white instantaneous precipitate was formed which was found to be very sparingly soluble in the solvent used. It was also found to be insoluble in acetonitrite and benzene. The substance decomposed and dissolved in water.

EXAMPLE 5

Preparation of phosphatidylcholine ethylene glycol dimethyl silyl chloride (I) (e)

$$Cl-\underset{\underset{CH_3}{|}}{\overset{\overset{CH_3}{|}}{Si}}-O(CH_2)_2-O-\underset{\underset{O^{\ominus}}{|}}{\overset{\overset{O}{\|}}{P}}-O(CH_2)_2\overset{\oplus}{N}(CH_3)_3$$

Ethylene glycol phosphatidylcholine (I) (c) (22.7 g; 0.1 mole) was added dropwise into thoroughly stirred dichlorodimethylsilane (129 g; 1.0 mole). External cooling was applied to keep the temperature at about 20° C.

The addition was completed in 30 minutes and the stirring was continued for another 30 minutes after which the mixture was freed from all volatile components (40° C.; 15 mm Hg) to obtain (I) (e) as dirty greyish gelatinous viscous liquid. The substance reacted with water with the evolution of hydrochloric acid.

EXAMPLE 6

Preparation of phosphatidylcholine ethanolamine (I) (f)

$$H_2N(CH_2)_2-O-\overset{O}{\underset{O^\ominus}{P}}-O(CH_2)_2\overset{\oplus}{N}(CH_3)_3$$

Choline acetate dichlorophosphate (28.1 g; 0.1 mole) was thoroughly stirred, cooled in an ice/salt bath and was treated very carefully with small drops of ethanolamine (61 g; 0.1 mole) over one hour. During this operation a slow stream of dried nitrogen was passed through the reaction vessel to remove the dense cloud formed. The mixture, after 10 minutes, settled into a reddish semisolid mass. It was then treated with dilute acetic acid (10% w/v, 100 ml) in which it failed to dissolve. A homogeneous solution, was however, obtained when it was allowed to react overnight. Volatile substances were evaporated (50°-60° C.; 15 mm Hg) and the residue was dissolved in methanol. It was then treated with solid sodium bicarbonate and the solid removed by filtration. The liquid was again freed from the volatile matter and the residue thus obtained (I) (f) was stored for 24 hours at 0.1 mm Hg, over $P_2O_5$.

EXAMPLE 7

Reaction of (I) (a) with i) glass ii) polyvinyl alcohol iii) polyhema and iv) cellulose acetate.

All of the above mentioned substances have free —OH groups on the surface.

A thin film of compound (I) (a) was applied to the materials named above. They were placed in a desiccator over $P_2O_5$ for up to 5 minutes after which the excess of the reagent was washed off with water followed by ethanol and sodium bicarbonate solution (5% w/v). They were washed with water again followed by alcohol and dried with warm air.

The procedure can be shown as an equation as follows:

$$\rangle\!-\!OH + Cl-\overset{O}{\underset{Cl}{\overset{\|}{P}}}-O(CH_2)_2\overset{\oplus}{N}(CH_3)_3 \xrightarrow{\overset{\ominus}{O}COCH_3} $$

$$\rangle\!-\!O-\overset{O}{\underset{O^\ominus}{\overset{\|}{P}}}-O(CH_2N(CH_3)_3)\overset{\overset{\ominus}{O}COCH_3}{\xrightarrow[\text{ii) NaHCO}_3]{\text{i) H}_2\text{O}}}$$

$$\rangle\!-\!O-\overset{O}{\underset{O^\ominus}{\overset{\|}{P}}}-O(CH_2)_2-\overset{\oplus}{N}(CH_3)_3$$

Treated polyvinyl alcohol, polyhema and cellulose acetate sheet gave positive ESCA analysis for phosphorus and nitrogen. The glass beads gave positive phosphate determinations by using untreated beads as reference.

EXAMPLE 8

Reaction of (I) (b) with i) glass and ii) cellulose acetate

The procedures followed for this treatment are given in Example 7.

Cellulose acetate and glass beads gave positive ESCA for phosphorus and nitrogen.

EXAMPLE 9

Reaction of (I) (e) with glass

The procedure followed for this treatment has already been given in Example 7.

Substance (I) (a) is superior to substances (I) (b) and (I) (e) when organic materials are required to be treated. The stability of the chemical bond obtained when (I) (a) is reacted with C—OH group is superior in stability and resembles those which occur naturally (for example in glycerophosphatidylcholine (GPC)). But the type of linkage (C—O—Si) obtained when (I) (b) and (I) (e) are treated with an organic OH group is less stable to hydrolysis. On the other hand compounds (I) (b) and (I) (e) are superior to (I) (a) when treatment of glass is required. The bond (Si—O—P) is susceptible to hydrolysis when (Ia) is used to treat glass surfaces.

EXAMPLE 10

Treatment of perspex with (I) (f)

The procedure can be shown as an equation as follows:

$$\rangle\!-\!COCl + H_2N(CH_2)_2-O-\overset{O}{\underset{O^\ominus}{\overset{\diagdown}{P}}}\!\!\diagup-O(CH_2)_2\overset{\oplus}{N}(CH_3)_3\rightarrow$$

$$\rangle\!-\!CONH-(CH_2)_2-O-\overset{O}{\underset{O^\ominus}{\overset{\|}{P}}}-O(CH_2)_2\overset{\oplus}{N}(CH_3)_3$$

Perspex surface was hydrolysed by stirring perspex pieces in 40% w/v aqueous KOH at 80° C. for 12 hours. Neutralisation of the above treated perspex with dilute hydrochloric acid generated free —COOH groups on the surface. These pieces were then placed in thionyl chloride for up to 5 seconds and while still wet with thionyl chloride, were dropped in a flask containing (I)(f). The contents of the flask were mixed thoroughly and the plastic pieces were recovered, washed with hot methanol, water and methanol again and dried in warm air.

EXAMPLE 11

Treatment of halogenated surfaces with (I)(d)

The procedure can be shown as an equation as follows:

$$\rangle\!-\!X + TlO-(CH_2)_2O-\overset{O}{\underset{O^\ominus}{\overset{\|}{P}}}-O(CH_2)_2\overset{\oplus}{N}(CH_3)_3\rightarrow$$

-continued

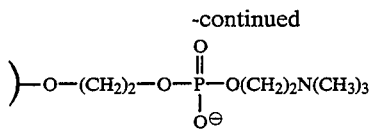

Clean polyvinyl chloride or PTFE pieces were added in a flask containing (I)(d) (produced from 6.22 g of thallous ethoxide) suspended in ethanol (50 ml) and acetonitrile (50 ml). The mixture was stirred and heated (30°–40° C.) under dried nitrogen for 48 hours (PTFE samples were heated for 96 hours). The plastic pieces were recovered and washed with distilled water and alcohol and dried.

EXAMPLE 12

Preparation of 2-chloro-2-oxo-1,2,3-oxazapholane

Phosphorus oxychloride (60 g; 0.39 mole) was diluted with anhydrous tetrahydrofuran (100 ml) cooled (0° C.) and treated with a dropwise addition of triethylamine (25 g) with vigorous stirring over 30 minutes. A gentle stream of dried nitrogen was passed through the stirred mixture, and with the temperature still maintained at 0° C. the mixture was treated with small drops of ethanolamine (23.92 g; 0.39 mole) over 30 minutes and then stirred for an additional one hour. Volatile matter was distilled (40° C.; 15 mm Hg) and the gumlike dark orange semisolid was extracted with dried nitromethane (4×40 ml). The nitromethane extract was concentrated free from the solvent (50° C.; 15 mm Hg) to obtain the required substance as dark red oil which was highly reactive towards water.

It was possible to use the freshly dissolved substance in nitromethane solution for coating the hydroxyl group containing surfaces (such as glass) but the compound became inactive when left for over 24 hours in nitromethane solution.

We claim:

1. A method for rendering a surface of a material biocompatible comprising the steps of (1) applying to said surface a compound of the formula

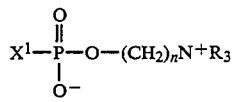

wherein $X^1$ is a reactive group which forms a covalent bond with a reactive group on said surface of said material to be rendered biocompatible, each R, which may be the same or different, is $C_1$–$C_4$ alkyl and n is 2, 3 or 4; and (2) reacting said compound and said reactive group on said surface under conditions such that the group $X^1$ forms a covalent linkage with said reactive group on said surface thereby rendering said surface biocompatible.

2. The method according to claim 1, wherein each R is methyl.
3. The method according to claim 1, wherein n is 2.
4. The method according to claim 2, wherein n is 2.
5. An article having a surface which is to be brought into contact with body fluids, cells, tissues or a human or animal body, wherein said surface has been rendered biocompatible by treatment with a compound of the formula

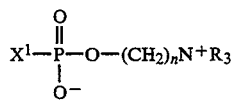

wherein $X^1$ is a reactive group which forms a covalent bond with a reactive group on said surface, and wherein each R, which may be the same or different, is $C_1$–$C_4$ alkyl and n is 2, 3 or 4.

6. The article according to claim 5, wherein each R is methyl.
7. The article according to claim 5, wherein n is 2.
8. The article according to claim 6, wherein n is 2.
9. Ethylene glycol phosphatidylcholine of the formula

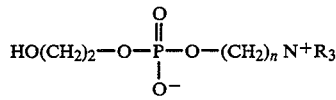

wherein each R is methyl and wherein n is 2.

* * * * *